United States Patent
Faulkner et al.

(10) Patent No.: US 9,119,392 B2
(45) Date of Patent: Sep. 1, 2015

(54) ARTICULATING ORGAN SUPPORT

(75) Inventors: Donald G. Faulkner, Charlotte, NC (US); John L. Robertson, Floyd, VA (US)

(73) Assignee: BioMedInnovations, LLC, Denver, NC (US)

( * ) Notice: Subject to any disclaimer, the term of this patent is extended or adjusted under 35 U.S.C. 154(b) by 886 days.

(21) Appl. No.: 12/942,497

(22) Filed: Nov. 9, 2010

(65) Prior Publication Data

US 2012/0116152 A1    May 10, 2012

(51) Int. Cl.
- *A61B 19/00* (2006.01)
- *A61F 2/00* (2006.01)
- *A61F 13/00* (2006.01)
- *A01N 1/00* (2006.01)
- *A01N 1/02* (2006.01)

(52) U.S. Cl.
CPC ............ *A01N 1/0242* (2013.01); *A01N 1/0247* (2013.01)

(58) Field of Classification Search
CPC ........................... A01N 1/0247; A01N 1/0242
USPC ................... 128/897–899; 600/37; 435/284.1
See application file for complete search history.

(56) References Cited

U.S. PATENT DOCUMENTS

| | | | |
|---|---|---|---|
| 5,586,438 A * | 12/1996 | Fahy | 62/78 |
| 6,977,140 B1 | 12/2005 | Owen et al. | |
| 8,317,677 B2 * | 11/2012 | Bertolote et al. | 600/37 |
| 8,329,450 B2 * | 12/2012 | Faulkner et al. | 435/284.1 |
| 2004/0235142 A1 | 11/2004 | Schein et al. | |
| 2005/0147958 A1 | 7/2005 | Hassanein et al. | |
| 2005/0255442 A1 * | 11/2005 | Brassil et al. | 435/1.2 |
| 2007/0049790 A1 * | 3/2007 | Wagner et al. | 600/37 |
| 2010/0028979 A1 * | 2/2010 | Faulkner et al. | 435/284.1 |
| 2010/0087843 A1 * | 4/2010 | Bertolote et al. | 606/157 |

FOREIGN PATENT DOCUMENTS

WO    2006118990    11/2006

* cited by examiner

*Primary Examiner* — John Lacyk
*Assistant Examiner* — Sunita Reddy
(74) *Attorney, Agent, or Firm* — Trego, Hines & Ladenheim, PLLC

(57) ABSTRACT

An organ support apparatus includes: an enclosure having a floor, opposed side walls, opposed end walls, and a lid; a first support pad disposed on the floor of the enclosure, the first support pad comprising a plurality of inflatable and flexible chambers; and an inflation apparatus coupled to the chambers and operable to individually inflate or deflate each chamber.

21 Claims, 6 Drawing Sheets

ARTICULATING ORGAN SUPPORT

BACKGROUND OF THE INVENTION

This invention relates generally to organ support and bypass processes, and more particularly to methods and apparatus for physically supporting an organ during such processes.

Numerous medical procedures require circulation of a fluid through an internal organ, optionally with treatment of the fluid by processes such as filtering, oxygenation, and the like. For example, when an organ is harvested from a donor for transplantation, a neutral saline solution is used to flush out the donor's blood from the blood vessels of the organ.

It is also known that some devices use a similar process to circulate an aqueous organ preservation fluid, such as "Belzer's solution", through organs which have been harvested for transplantation. This action sustains the organ while it is outside the body by attempting to preserve functioning, and increases the limited "shelf life" of transplant organs compared to conventional chilled storage.

More advanced concepts provide methods and apparatus for supporting an organ (in vivo or in vitro) in a manner which closely mimics biological processes by providing carefully controlled fluid pressure and chemical profiles. One such concept is described in published U.S. patent application 2010/0028979 entitled "Methods And Apparatus For Organ Support".

All of these processes and devices require that an internal organ be physically supported outside the body, typically in a rigid or resilient static container. Thus supported, gravity forces on the organ tend to press it against whatever support is used underneath it, resulting in localized pressure on its lower and lateral surfaces. This can result in localized pressure ischemia, cellular damage and/or loss of organ function and vitality.

BRIEF SUMMARY OF THE INVENTION

These and other shortcomings of the prior art are addressed by the present invention, which provides an articulating organ support.

According to one aspect of the invention, an organ support apparatus includes: an enclosure having a floor, opposed side walls, opposed end walls, and a lid; a first support pad disposed on the floor of the enclosure, the first support pad comprising a plurality of inflatable and flexible chambers; and an inflation apparatus coupled to the chambers and operable to individually inflate or deflate each chamber.

According to another aspect of the invention, a method for supporting an organ, includes: providing an enclosure adapted to contain an organ; placing the organ on a first support pad disposed on a floor of the enclosure, the first support pad comprising a plurality of inflatable and flexible chambers; and selectively inflating and deflating the chambers to provide a time-varying contact pressure profile with the organ.

According to yet another aspect of the invention, a method for supporting an organ includes: providing an enclosure adapted to contain an organ, the enclosure having a floor opposite a lid; placing a first support pad against the floor, the first support pad comprising a plurality of inflatable and flexible chambers; placing a second support pad against the lid, the second support pad comprising a plurality of inflatable chambers; placing the organ between the first and second support pads; inflating the chambers to clamp the organ in position between the support pads; and selectively tilting or rotating the enclosure to provide a time-varying contact pressure profile between the first and second support pads and the organ.

BRIEF DESCRIPTION OF THE DRAWINGS

The invention may be best understood by reference to the following description taken in conjunction with the accompanying drawing figures in which.

DETAILED DESCRIPTION OF THE INVENTION

Figure 1:
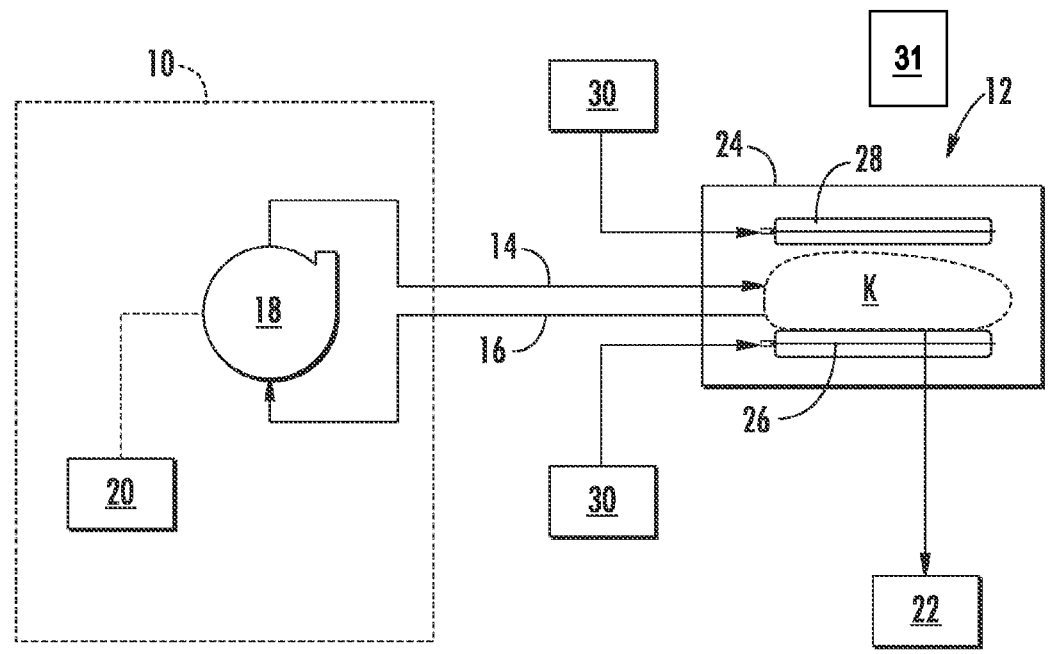
FIG. 1 is a schematic view of an organ support apparatus constructed according to an aspect of the present invention, coupled to a perfusion system.

Referring to the drawings wherein identical reference numerals denote the same elements throughout the various views, FIG. 1 depicts diagrammatically a perfusion system 10 suitable for circulating a fluid through an organ, in conjunction with an organ support apparatus 12 which is constructed in accordance with the present invention. As used herein the term "perfusion system" broadly refers to any apparatus which functions to circulate fluid through an organ and could range from a simple saline flushing device to a highly sophisticated organ support apparatus such as the one described in U.S. published patent application 2010/0028979 entitled "Methods And Apparatus For Organ Support". The perfusion system 10 comprises a fluid circuit defined by plastic tubing or another suitable type of conduit, connected to an organ, depicted generally at "K", by an inlet line 14 and an outlet line 16.

The perfusion system 10 includes some means for circulating fluid, such as a pump, along with appropriate fluid treatment equipment, such as one or more filters, heat exchangers, oxygenators, de-aerators, or chemical injectors. All of this equipment is depicted schematically at number 18. An electronic controller 20 may be used to control the operation of the perfusion system 10. The illustrated example is explained in the context of providing support for a kidney K which is contained in the organ support apparatus 12 and connected to a fluid collection container 22 which receives a fluid flow from the kidney K. However, it will be understood that the principles of the present invention are broadly applicable to support of many types of organs. The fluid collection container 22 may not be needed for other organs.

The basic components of the organ support apparatus 12 are an enclosure 24, a lower support pad 26, an optional upper support pad 28, and an inflation apparatus 30.

Optionally, an imaging device 31 (such as a camera operating in the visual, UV, or IR frequency ranges) may be used to observe the condition of the organ K through the enclosure 24. One example of a suitable imaging device is a confocal microscope such as the VIVASCOPE device available from Lucid, Inc., Rochester, N.Y. 14623 USA. Positioning apparatus (not shown) capable of multi-axis positioning may be provided to point the imaging device 31 at a particular target area of the organ K.

Figure 2:
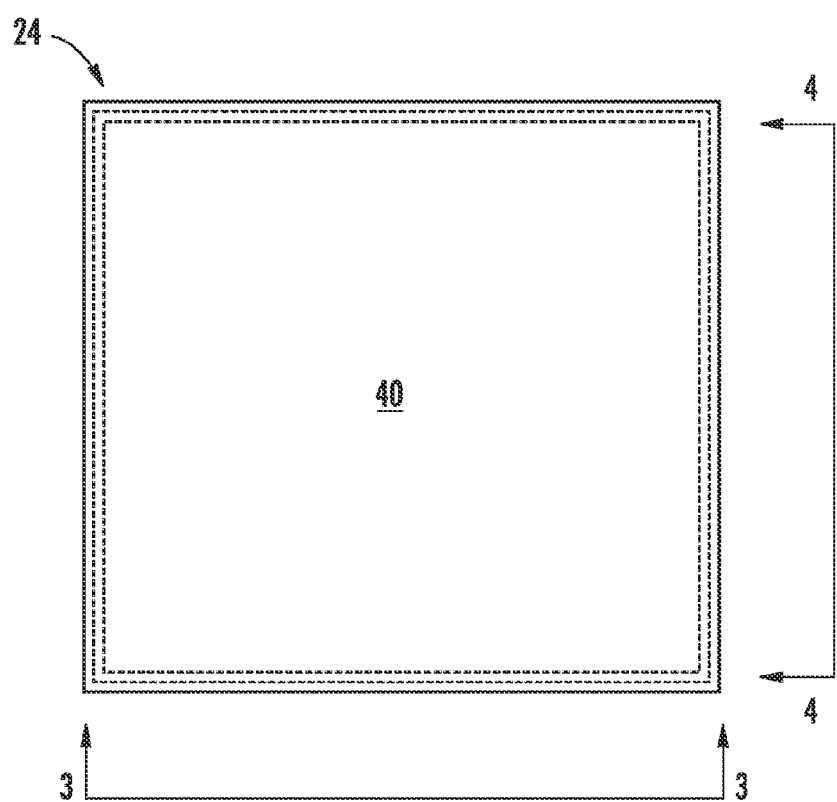
FIG. 2 is top view of the organ support apparatus of FIG. 1.
Figure 3:
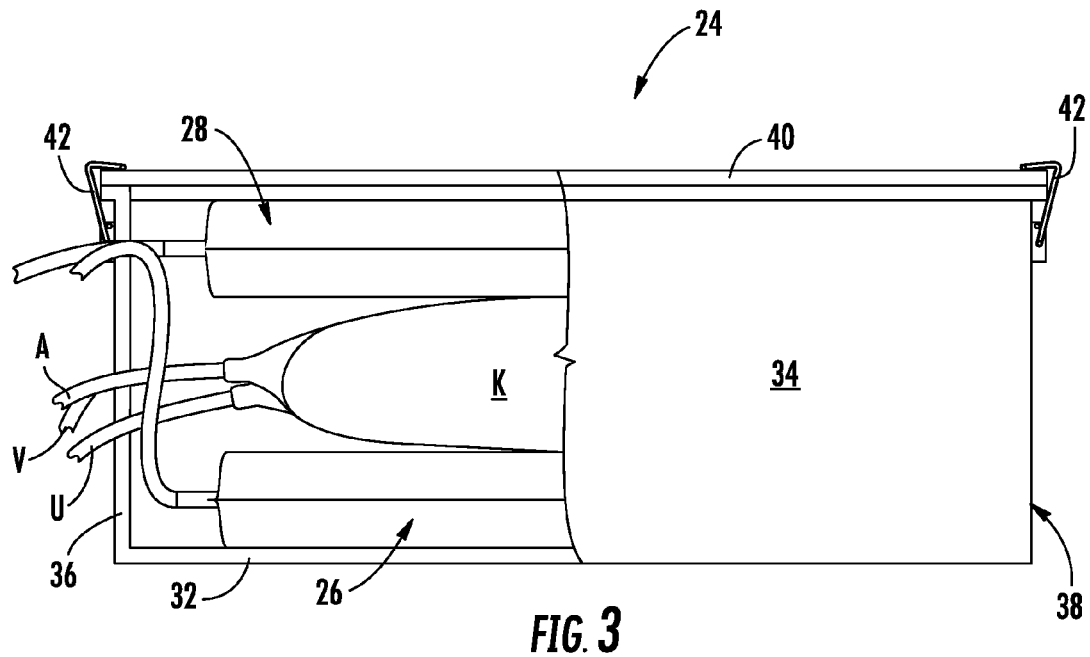
FIG. 3 is a partially-sectioned side view of the organ support of FIG. 2.
Figure 4:
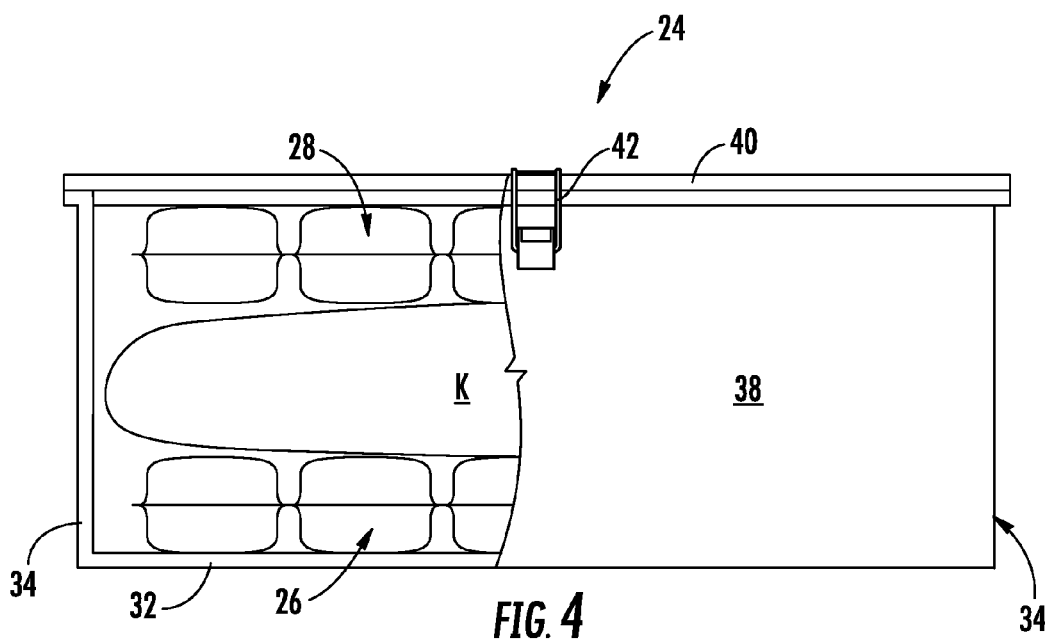
FIG. 4 is a partially-sectioned end view of the organ support of FIG. 2.
Figure 5:
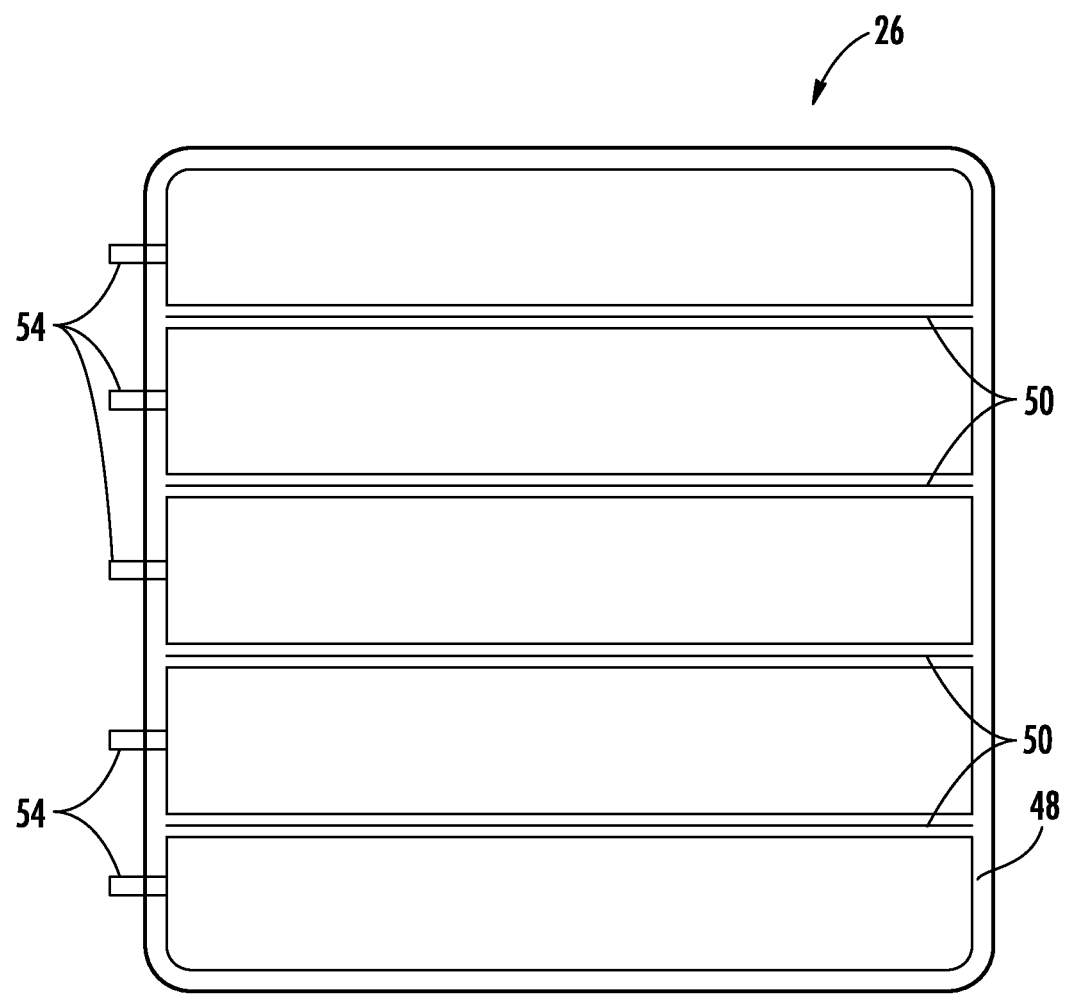
FIG. 5 is a top view of a support pad of the organ support apparatus.
Figure 6:
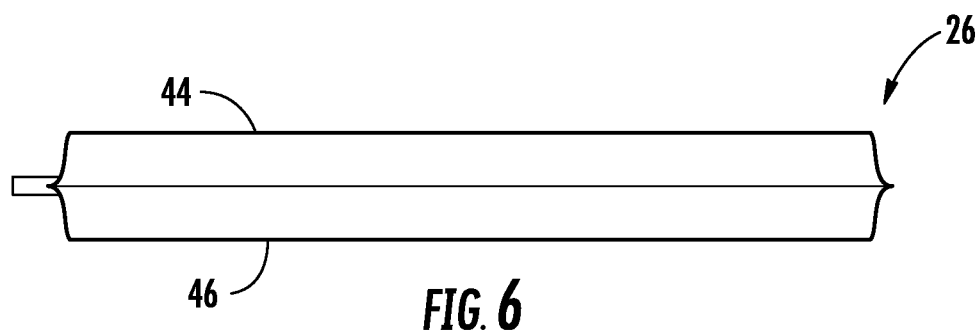
FIG. 6 is a side view of the support pad of FIG. 5.
Figure 7:
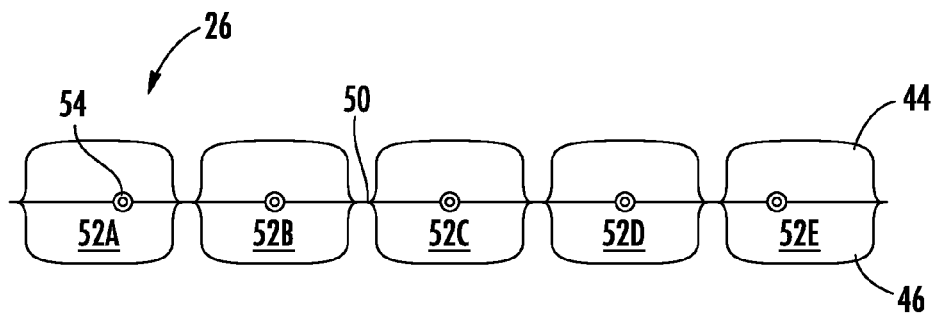
FIG. 7 is a front end view of the support pad of FIG. 5.
Figure 8:
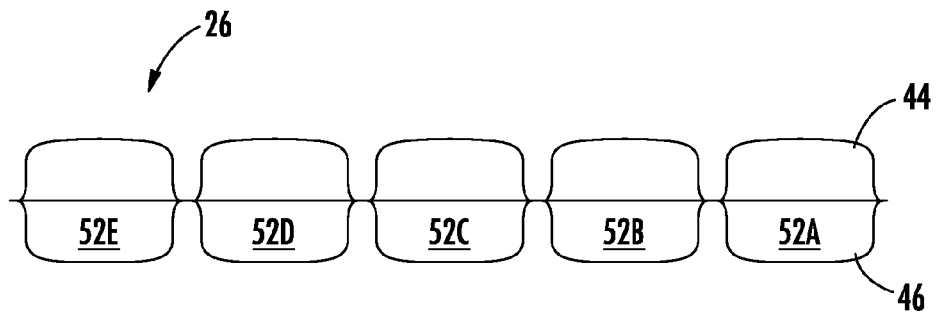
FIG. 8 is a rear end view of the support pad of FIG. 5.

FIGS. 2-4 illustrate the organ support apparatus 12 in more detail. The organ enclosure 24 provides physical protection to the organ K and isolates it from the external environment. Preferably the material of the enclosure 24 is transparent to visible light and/or other select portions of the radio frequency ("RF") spectrum to facilitate imaging of the organ K. For example, it may be constructed from a material such as sterilizable transparent medical-grade polymer. As illustrated it is in the form of a rectangular box with a floor 32, side walls 34, front and rear walls 36 and 38, and a removable lid 40. The lid 40 may be secured with latches 42. The front wall 36 is provided with pass-through openings for making connections between the artery "A" and vein "V" of the kidney K (for example) and the inlet and outlet lines 14 and 16 respectively of the perfusion system 10. There is also a pass-through opening for making a connection to the ureter U, to allow urine to drain to the fluid collection container 22 (see FIG. 1).

The lower support pad 26 rests on the floor 32 and the organ K rests on top of the lower support pad 26. The lower support pad 26 shown in more detail in FIGS. 5-8. It is constructed from a top sheet 44 and a bottom sheet 46 which are selectively bonded together along their mutual peripheral edges 48 and along dividing seams 50. The remaining unbonded portions define individual inflatable and flexible chambers 52A through 52E. The sheets 44 and 46 may be made from any flexible, fluid-tight material, such as polymers, treated fabrics, or rubber. Preferably the material is transparent to visible light and/or other select portions of the radio frequency ("RF") spectrum to facilitate imaging of the organ K. The sheets 44 and 46 may be bonded together by any method which provides a leak-tight connection, such as by thermal or ultrasonic bonding, adhesives, or crimping.

In the illustrated example, there are five side-by-side, elongated, generally rectangular chambers 52A through 52E. As will be explained further below, the shape, number, and configuration of the chambers 52A through 52E is not critical and could be varied in a number of ways to suit a particular application. For example, various patterns of elongate shapes, grid patterns, and/or arcs or circles could be used to define the chambers. A fluid connection is provided to each of the individual chambers 52A-52E. As shown, individual tube fittings 54 are employed.

If used, the upper support pad 28 would be identical in construction to the lower support pad 26. The upper support pad 28 would be placed between the organ K and the lid 40.

Figure 9:
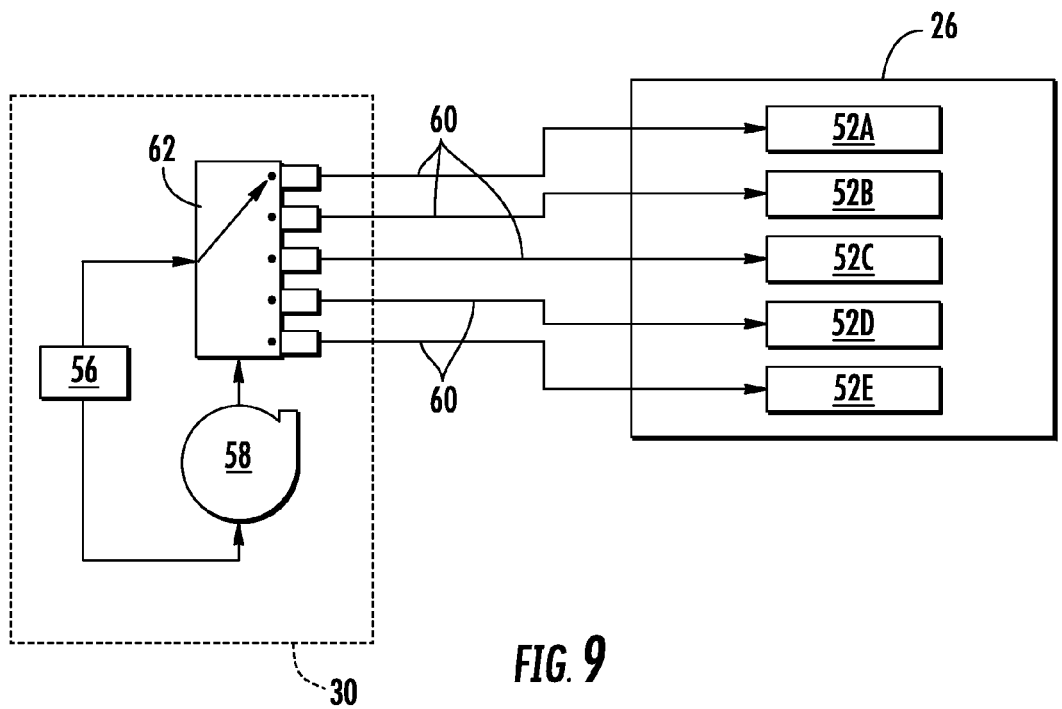
FIG. 9 is a schematic diagram of a support pad coupled to an inflation apparatus.

An inflation apparatus (shown schematically at 30 in FIG. 1) is provided for selectively inflating and deflating each chamber 52A-52E. FIG. 9 shows an example of the inflation apparatus 30 in a basic form comprising a controller 56 coupled to an air pump 58 which is in turn coupled to the individual chambers 52A-52E of the lower support pad 26 through tubes 60. Water or another liquid could be used instead of air. The pump 56 may be a pressure pump only, or it may be a combination pressure/vacuum pump to provide for improved deflation. The controller 56 may be a general-purpose microcomputer of a known type, such as a PC-based computer, or it may be a custom processor, or may incorporate one or more programmable logic controllers (PLC). Depending on the type of perfusion system 10, the pump 58 may be controlled through software programming integrated into the perfusion system controller 20 (see FIG. 1). As shown in FIG. 9, the pump 58 is connected to the chambers 52A-52E through a multi-port remotely-controlled valve 62 whose position is commanded by the controller 56. Alternatively, an independent pump could be provided for each chamber 52A-52E. If an upper support pad 28 is used, a separate inflation apparatus 30 (see FIG. 1) may be provided for it, or the valve 62 could be modified to accommodate additional chambers of the upper support pad 28.

Figure 10:
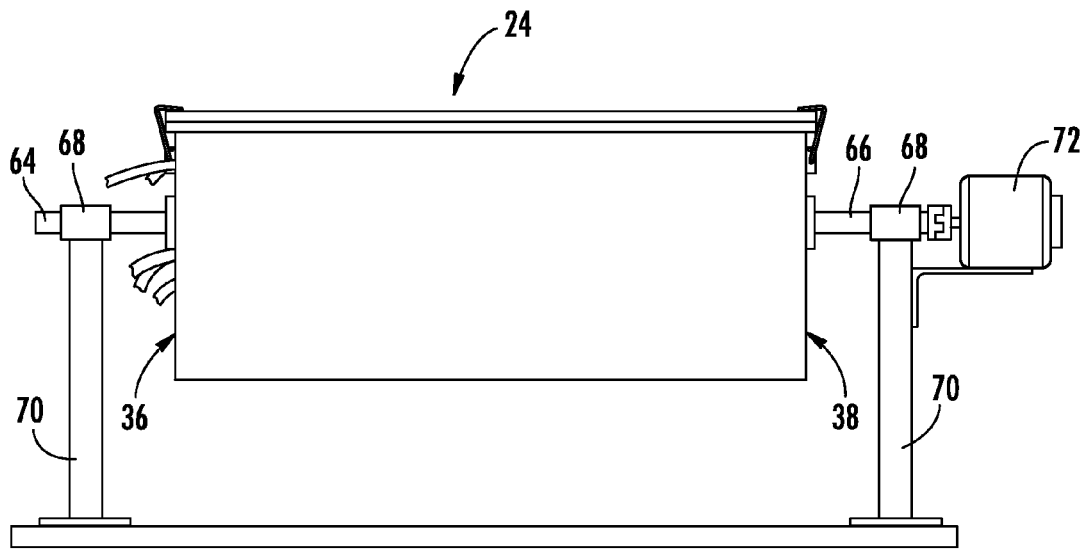
FIG. 10 is a side view of an organ support apparatus including a rotation apparatus.
Figure 11:
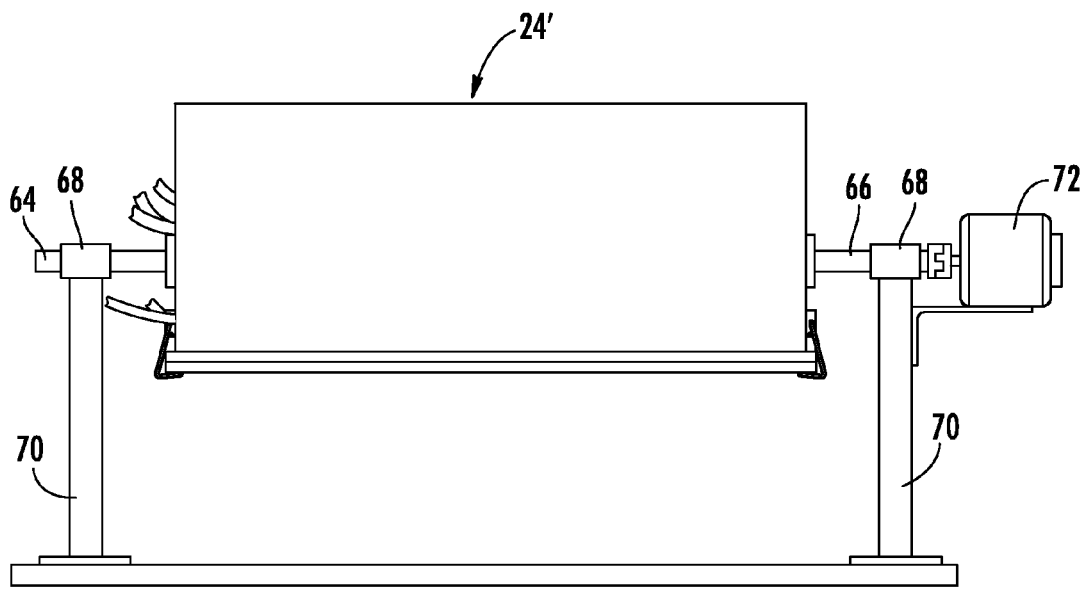
FIG. 11 is a side view of the organ support apparatus of FIG. 10 in an inverted position.

Optionally, the capabilities of the support apparatus 12 may be further extended by providing apparatus for pivoting or rotating the enclosure 24. FIG. 10 illustrates an enclosure 24 with shafts 64 and 66 extending from the front and rear walls 36 and 38, respectively, and mounted in pivot bearings 68 which are in turn held by stands 70. An electric motor 72 (for example a stepper motor), or other suitable type of rotary device, is coupled to one of the shafts 64 or 66. Rotation of the shaft of the motor 72 pivots the enclosure 24 about the shafts 64 and 66. This function may be used to tilt the organ K (not seen in FIGS. 10 and 11) to specific angles or to periodically invert it during a perfusion procedure (the inverted position is shown in FIG. 11). If desired, a multi-axis gimbal of a known type may be employed to mount the enclosure 24 so that it may be rotated about more than one axis.

Figure 12:
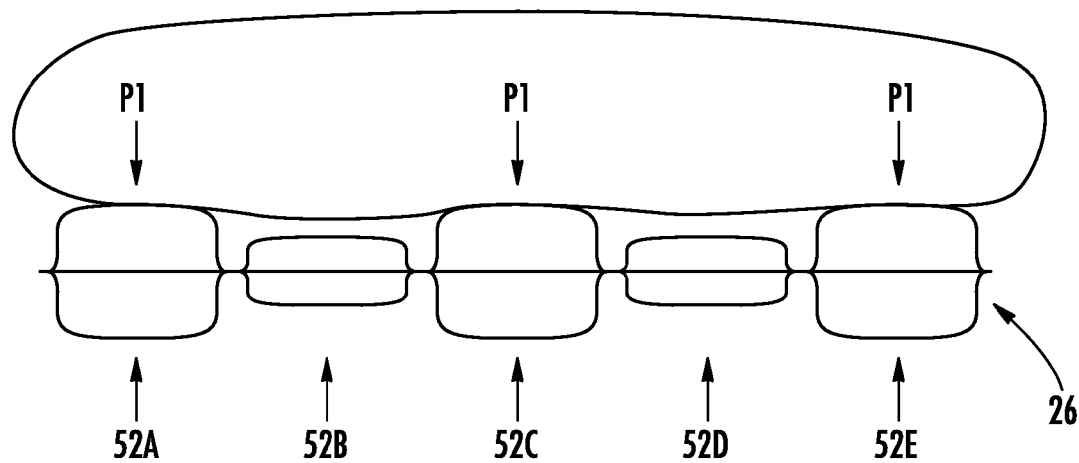
FIG. 12 is a schematic end view of a support pad in a first configuration.
Figure 13:
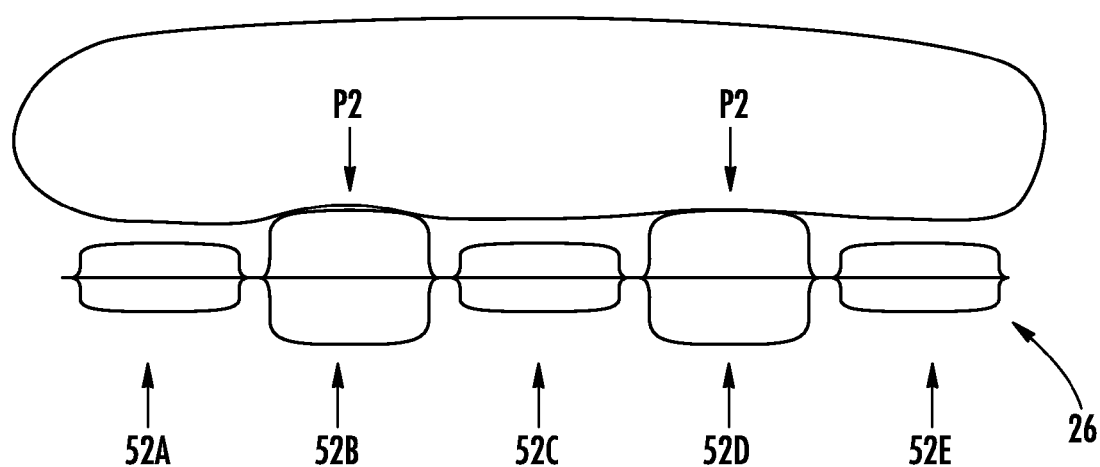
FIG. 13 is a schematic end view of a support pad in a second configuration.

The operation of the organ support apparatus 12 will be described with reference to FIGS. 12 and 13. An organ K is placed on the lower support pad 26 within the enclosure 24. The organ K is connected to the perfusion system 10 which is placed in operation circulating fluid through the organ K. While the organ K is resting on the lower support pad 26, the chambers 52A-52E are selectively inflated and deflated so as to provide a varying contact pressure profile with the organ K. For example, FIG. 12 shows chambers 52A, 52C, and 52E as being fully inflated while chambers 52B and 52D are deflated. In this configuration the organ K is supported along three spaced-apart lines, and points of relatively higher pressure are present at the locations marked with arrows "P1". At a subsequent time, chambers 52B and 52D may be fully inflated while chambers 52A, 52C, and 52E are deflated. This configuration is shown in FIG. 13. The organ K would thus be supported along two spaced-apart lines and points of relatively higher contact pressure are present at the locations marked with arrows "P2". The locations P1 are relieved of pressure, allowing free flow of circulation and absence of mechanical stress. This cycle of alternating inflation and deflation may be repeated as often as necessary so that no one portion of the organ K is subjected to damaging pressure for too long, which could result in localized pressure ischemia. For example, the pressure in any one location may be relieved about 2 or 3 times per minute.

If the rotation apparatus described above are used, then the enclosure 24 with the organ K may be periodically tilted and/or inverted so that contact pressures on the organ K are shared between its opposite surfaces. For example, the organ K may be tilted and/or inverted with a frequency of about once per minute to about once every 30 minutes. The frequency is subject to the vascular resistance and condition of the organ K or tissue. The tilt and/or inversion may be in addition to or as an alternative to the selective inflation and deflation of the chambers 52A-52E. The imaging device 31, such as a scanning high resolution infrared camera may be employed to take a series of images and build therefrom a mosaic image of the organ K for localized and global comparison. For example, the organ K may be imaged in small blocks, e.g. 20 mm×20 mm (0.8 in.×0.8 in.). In the image, ischemic areas will exhibit relatively higher or lower temperatures than the surrounding tissue.

In response to the detection of such areas, the controller 56 may be programmed to tilt and/or invert the organ enclosure 24, and/or to selectively inflate or deflate the chambers 52A-52E. To facilitate the imaging and control process, the temperature of the fluid circulating through the organ K may be altered (e.g. using the perfusion system 10) slightly up and down from a physiologically suitable temperature for organ characterization and preservation. For example, the fluid temperature change may be plus or minus about 2 degrees C. (plus or minus about 3.6 degrees F.) Any ischemic areas will respond to the fluid temperature change at a substantially slower rate than the surrounding tissue, resulting in hot or cold spots which can be detected by the imaging device 31.

The upper support pad 28 may be used to supplement the lower support pad 26. For example, if the enclosure 24 is inverted, then the organ K would rest on the upper support pad 28 and the alternate chamber inflation cycle described above would be carried out using the upper support pad 28. The upper support pad 28 may also be used simultaneously with the lower support pad 26 to provide a gentle clamping action to the organ K in order to support it during tilting and/or inversion, or during movement or transport of the enclosure 24.

The foregoing has described an organ support apparatus and methods for its operation. While specific embodiments of the present invention have been described, it will be apparent to those skilled in the art that various modifications thereto can be made without departing from the spirit and scope of the invention. Accordingly, the foregoing description of the preferred embodiment of the invention and the best mode for practicing the invention are provided for the purpose of illustration only and not for the purpose of limitation.

What is claimed is:

1. An organ support apparatus, comprising:
   a housing having a floor, opposed side walls, opposed end walls, and a lid, the housing adapted to completely encompass an organ placed entirely within the housing;
   a first support pad disposed on the floor of the housing, the first support pad comprising a plurality of inflatable and flexible chambers; and
   an inflation apparatus coupled to the chambers and operable to individually inflate or deflate each chamber.

2. The apparatus of claim 1 wherein the first support pad comprises flexible, fluid-tight top and bottom sheets bonded together along mutual peripheral edges and seams such that unbonded portions of the top and bottom sheets define the chambers.

3. The apparatus of claim 2 wherein the plurality of chambers are elongated, and arranged in a side-by-side configuration.

4. The apparatus of claim 1 further comprising a second support pad disposed within the housing opposite the first support pad, the second support pad comprising a plurality of inflatable chambers.

5. The apparatus of claim 4 wherein the second support pad comprises flexible, fluid-tight top and bottom sheets bonded together along mutual peripheral edges and seams such that unbonded portions of the top and bottom sheets define the chambers.

6. The apparatus of claim 5 wherein the second support pad comprises a plurality of elongated, side-by-side chambers.

7. The apparatus of claim 1 wherein the inflation apparatus comprises:
   a pump;
   a multi-port valve coupled to the pump and to each of the chambers, the valve adapted to selectively couple the pump to a selected one of the chambers; and
   an electronic controller operably coupled to the pump and the valve.

8. The apparatus of claim 1 further comprising a rotation apparatus operable to rotate the housing about an axis.

9. The apparatus of claim 8 further comprising an imaging device positioned so that the housing is within a field of view thereof, the imaging device operably connected to the rotation apparatus.

10. The apparatus of claim 8 wherein the housing is mounted for rotation about a pair of shafts and wherein an electric motor is mechanically coupled to at least one of the shafts.

11. The apparatus of claim 1 further comprising an imaging device positioned so that the housing is within a field of view thereof, the imaging device operably connected to the inflation apparatus.

12. A method for supporting an organ, comprising:
   providing a housing having a floor, opposed side walls, opposed end walls, and a lid, the housing adapted to completely encompass an organ placed entirely within the housing;
   placing the organ on a first support pad disposed on a floor of the enclosure, the first support pad comprising a plurality of inflatable and flexible chambers; and
   repeatedly inflating and/or deflating one or more of the chambers so as to provide a time-varying contact pressure profile with the organ, the time-varying contact pressure profile selected such that no one portion of the organ is subjected to damaging pressure long enough to cause localized pressure ischemia in that portion.

13. The method of claim 12 wherein the first support pad comprises a plurality of elongated, side-by-side chambers, the method further comprising cyclically inflating and deflating alternate ones of the chambers.

14. The method of claim 12 further comprising periodically rotating the housing about an axis so as to invert the organ.

15. The method of claim 12 further comprising placing a second support pad placing between the organ and a lid of the housing which is disposed opposite the floor, the second support pad comprising a plurality of inflatable chambers; and selectively inflating and deflating the chambers to provide a varying contact pressure profile with the organ.

16. The method of claim 15 wherein the second support pad comprises a plurality of elongated, side-by-side chambers, the method further comprising cyclically inflating and deflating alternate ones of the chambers of the second support pad.

17. The method of claim 12 further comprising:
   using an imaging device, observing the organ within the housing and identifying at least one portion of the organ having a temperature different from the surrounding tissue of the organ; and
   selectively inflating and deflating the chambers so as to relieve the pressure applied to the identified portion.

18. The method of claim 17, wherein the imaging device is used to generate a plurality of images of varying locations of the organ which are then assembled so as to form a mosaic image.

19. The method of claim 17 further comprising:

prior to observing the organ, maintaining the organ at a first temperature; and changing the temperature of the organ by a selected amount.

20. A method for supporting an organ, comprising:

providing a housing having a floor, opposed side walls, opposed end walls, and a lid, the housing adapted to completely encompass an organ placed entirely within the housing;

placing a first support pad against the floor, the first support pad comprising a plurality of inflatable and flexible chambers;

placing a second support pad against the lid, the second support pad comprising a plurality of inflatable chambers;

placing the organ between the first and second support pads;

inflating the chambers to clamp the organ in position between the support pads; and selectively tilting or rotating the housing to provide a time-varying contact pressure profile between the first and second support pads and the organ.

21. The method of claim 20 further comprising:

using an imaging device, observing the organ within the housing and identifying at least one portion of the organ having a temperature different from the surrounding tissue of the organ; and selectively tilting or rotating the housing so as to relieve the pressure applied to the identified portion.

* * * * *